US008193180B2

(12) United States Patent
Brard et al.

(10) Patent No.: US 8,193,180 B2
(45) Date of Patent: Jun. 5, 2012

(54) N-AMINO TETRAHYDROTHIAZINE DERIVATIVES, METHOD OF MANUFACTURE AND USE

(75) Inventors: Laurent Brard, Seekonk, MA (US); Rakesh Kumar Singh, Barrington, RI (US); Kyu Kwang Kim, Warwick, RI (US); Giselle Saulnier-Sholler, Charlotte, VT (US)

(73) Assignee: Women & Infants Hospital, Providence, RI (US)

( * ) Notice: Subject to any disclaimer, the term of this patent is extended or adjusted under 35 U.S.C. 154(b) by 222 days.

(21) Appl. No.: 12/524,435

(22) PCT Filed: Jan. 23, 2008

(86) PCT No.: PCT/US2008/051794
§ 371 (c)(1),
(2), (4) Date: Mar. 4, 2010

(87) PCT Pub. No.: WO2008/091946
PCT Pub. Date: Jul. 31, 2008

(65) Prior Publication Data
US 2010/0179136 A1    Jul. 15, 2010

Related U.S. Application Data

(60) Provisional application No. 60/897,116, filed on Jan. 24, 2007.

(51) Int. Cl.
*C07D 417/12* (2006.01)
*A61K 31/541* (2006.01)

(52) U.S. Cl. .................. 514/228.2; 544/58.6; 544/58.7
(58) Field of Classification Search ................ 544/58.6, 544/58.7; 514/228.2
See application file for complete search history.

(56) References Cited

U.S. PATENT DOCUMENTS

| 3,682,902 A | 8/1972 | Oertel |
| 3,884,913 A | 5/1975 | Winkelmann |
| 3,943,098 A | 3/1976 | Rody |
| 3,989,690 A | 11/1976 | Verge |
| 4,071,528 A | 1/1978 | Dalton |

OTHER PUBLICATIONS

Saulnieh Shulleh, "Antitumor, activity of nifurtimox etc.," J. Ped. Hematol./Oncology, p. 693-95, Oct. 1, 2006, abst.
Asinger, "Aur Kenntnis der Readtionsfahigkeit etc," Monatshefte fur chemie 112:643-57(1981).
Asingeh, "Zur Kenntnis der Reaktionsfanigkeit des Thiomorpholins etc," Monatshefte fur chemie 111:385-98(1980).
Shridhar, "Coumarin derivatives etc," J. Indian Chem. Soc. 56(1):48-51 (1979), abst.
Bock, "The sructure-activity relationship etc," Arzneimtiiel Forschung 22:1564-69(1972).

*Primary Examiner* — Kahsay T Habte
(74) *Attorney, Agent, or Firm* — Cserr IP Strategies

(57) ABSTRACT

This invention comprises the innovative synthesis of N-amino tetrahydrothiazine free bases and their salts. This invention further comprises the use of the derivatives and their therapeutic application as anticancer agents. Further this invention comprises their manufacture and use.

18 Claims, 4 Drawing Sheets

N-AMINO TETRAHYDROTHIAZINE DERIVATIVES, METHOD OF MANUFACTURE AND USE

CROSS REFERENCES TO RELATED APPLICATIONS

This application is a national phase application of, and claims priority to, PCT/CA2008/051794, filed on Jan. 23, 2008, which claims the benefit of priority under 35 U.S.C. §119(e) to U.S. Patent Application No. 60/897,116 filed on Jan. 27, 2007, the disclosures of which are incorporated herein by reference.

FIELD OF THE INVENTION

This invention comprises an innovative synthesis of non-nifurtimox derivatives of N-amino tetrahydrothiazine free base, salts and their derivatives. This invention further comprises therapeutic applications of these compounds. Further included are methods of using these N-amino tetrahydrothiazine free bases, salts and their derivatives.

BACKGROUND OF THE INVENTION

N-amino tetrahydrothiazine derivatives, also termed N-substituted thiomorpholine, such as nifurtimox are the mainstay drug therapy for Chagas disease, caused by a protozoan parasite (*Trypanosoma cruzi*).

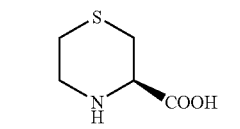

1,4 thiazane-(3S)-carboxylic acid

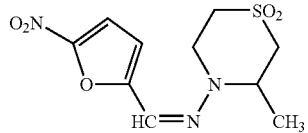

Nifurtimox

Nifurtimox has recently been reported to have an anticancer therapeutic activity. However, nifurtimox and other nitro derivatives reportedly have a low efficacy of cancer cell inhibition.

BRIEF DESCRIPTION OF THE INVENTION

It has now been discovered that a modified nifurtimox scaffold is a therapeutically effective inhibitor of cancer cells. These derivatives exhibited potent anti-cancer activity against human neuroblastoma cells in an in-vitro assay, and were characterized using NMR and Mass spectrometry.

This invention comprises a family of non-nifurtimox derivatives of N-amino tetrahydrothiazine including sulfoxide and sulfone analogs. Also included are imine, amine and both mono and disubstituted amino derivatives.

The invention also comprises methods of use of these N-amino tetrahydrothiazine derivatives as de-novo drugs and/or analogs serving as antineoplastics, anti-angiogenics, free-radical modulators, antibacterials, antiprotozoals, antifungals, antivirals, anti-MDRs (multi-drug resistance), anti-reflux agents, anti-hyperglycemics, antimalerials, neurotransmitters/CNS modulators, antilipidemics, and as potent anti-inflammatory agents. Particular embodiments of this invention include the treatment of Neuroblastoma, Medulloblastoma, and Alzheimer's disease.

In addition, this invention provides compositions and methods that are useful for the prevention of chemical carcinogenesis and alterations of drug metabolism involving epoxides, free oxygen radicals or intermediates thereof. These compositions are useful for moderating or preventing oxidative damage in human transplant organs, and for inhibiting reoxygenation or reperfusion injuries following the reperfusion of ischemic tissues.

It has now been discovered that N-amino tetrahydrothiazine derivatives display anticancer activity. This has been demonstrated in vitro in various cultured solid tumor neuroblastoma, medulloblastoma, and ovarian cancer cells. A similar effect is anticipated for cancers of the breast, prostate, pancreatic, vulva, and liver, as well as in other non-solid human tumors.

This invention includes compounds having the formulae (I) through (VI):

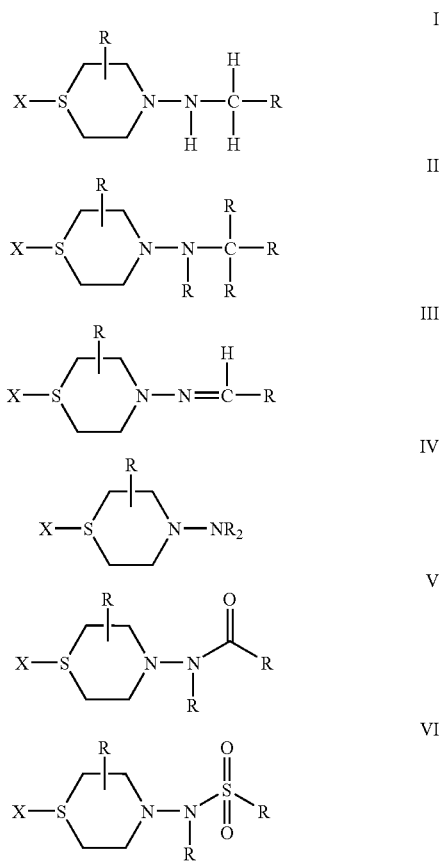

"X" is O, O$_2$ or absent.
R is selected independently from hydrogen, alkyl, aryl, heteroaryl, alkylaryl, arylalkyl, alkenyl, alkynyl, amino, hydroxyl, halogens, acids, amides, reverse amides, acyls, carbamates, ureas, or thioureas, esters, aldehydes, NHC(=O)R$^1$x, NR$^1$xR$^2$x, —NHC(=O)NR$^1$xR$^2$x, C(=O)aryl, C(=O) heteroaryl, C(=O) heterocyclylalkyaryl, C(=O)alkyl, —OC(=O) NR$^1$xR$^2$x, [where R$^1$ and R$^2$ are independently hydrogen, alkyl, aryl, aryl alkyl and x is independently integers 1 or 2], NO$_2$, sulphonyls and/or derivatives such as chloride, amides, sulphonic acids, phosphates and nitriles. The derivatives of acids such as hydroxamates, hydrazides are also included herein except as to formula III wherein the imine R group cannot be 2-nitrofuran. It is further contemplated that additional substituents may be constructed onto a basic organometallic complex with equivalent or improved activity. By "independently" it is meant that the identity of one "R" does not limit or dictate the identity of any other R.

Substituents described herein can be combined with at least one other substituent selected from the group above or with other reagents or intermediates to form cyclic ring structures, and fused ring structures with or without heteroatom(s).

The substituents defined as R could be further derivatized, using standard organic synthetic methods. One such example is the conversion of nitrile groups to tetrazoles with sodium azide. Isosteric and bioisoteric replacements are also encompassed within the scope of this invention. One such example is the replacement of an acid functionality with a tetrazole. Other examples are the replacement of a phenyl ring with a thiophene ring and/or replacement of a hydrogen atom with fluorine atom.

In some embodiments, substituents represented by R are further substituted by replacing one or more atoms with the groups consisting of piperazine, piperidine, peptidic bonds, alkyl, aryl, arylalkyl, fused, saturated, half saturated two or four carbocyclic or heterocyclic rings and sugars.

Particular compounds of the present invention include

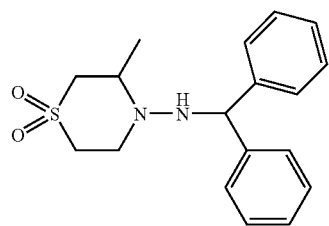

with the proposed systematic name N-(3-methyl-1,1-dioxo-1,4-thiazinan-4-yl)-1-[1,1-diphenyl]methane;

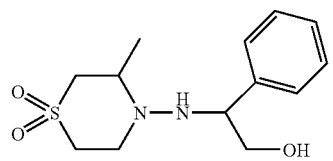

with the proposed systematic name N-(3-methyl-1,1-dioxo-1,4-thiazinan-4-yl)-1-[1-phenyl, 1-methanol]methane;

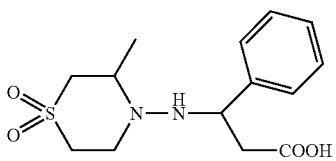

with the proposed systematic name N-(3-methyl-1,1-dioxo-1,4-thiazinan-4-yl)-1-[1-phenyl, 1-acetic acid]methane;

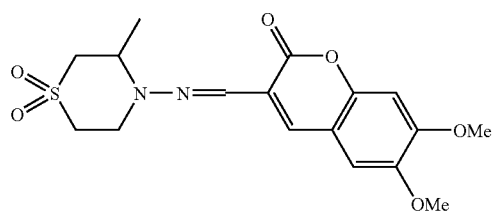

with the proposed systematic name N-(3-methyl-1,1-dioxo-1,4-thiazinan-4-yl)-1-[5,6-dimethoxy coumarin-2-yl]methanimine;

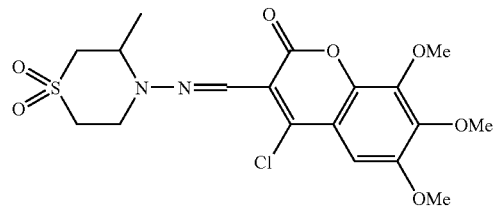

with the proposed systematic name N-(3-methyl-1,1-dioxo-1,4-thiazinan-4-yl)-1-[3-chloro, 5,6,7-trimethoxy coumarin-2-ly]methanimine;

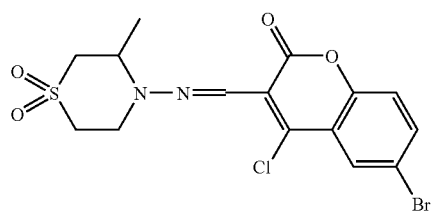

with the proposed systematic name N-(3-methyl-1,1-dioxo-1,4-thiazinan-4-yl)-1-[3-chloro,5-bromo coumarin-2-ly]methanimine, also named RKS-2-62;

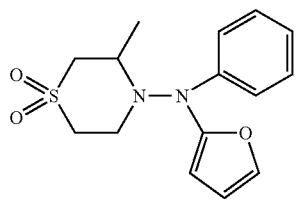

with the proposed systematic name N-(3-methyl-1,1-dioxo-1,4-thiazinan-4-yl)-1-[1-phenyl, 1-furan-2-yl];

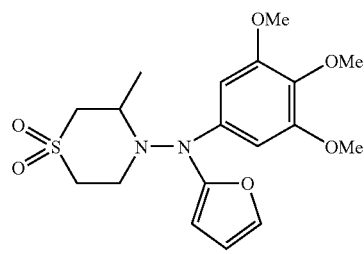

with the proposed systematic name N-(3-methyl-1-oxo-1,4-thiazinan-4-yl)-1-[1-(3,4,5-trimethoxy phenyl), 1-furan-2-ly];

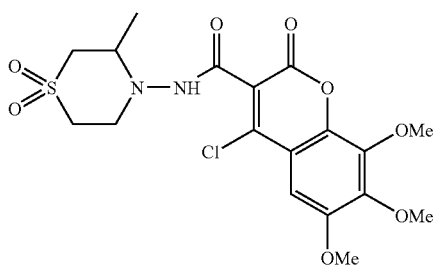

with the proposed systematic name N-(3-methyl-1,1-dioxo-1,4-thiazinan-4-yl)-1-(3-chloro, 5,6,7-trimethoxy coumarin-2-carbonyl];

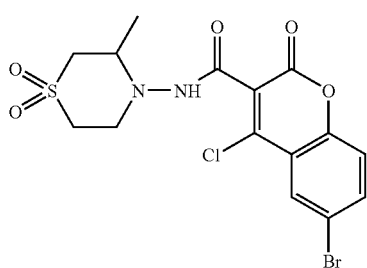

with the proposed systematic name N-(3-methyl-1,1-dioxo-1,4-thiazinan-4-yl)-1-(3-chloro,5-bromo coumarin-2-carbonyl];

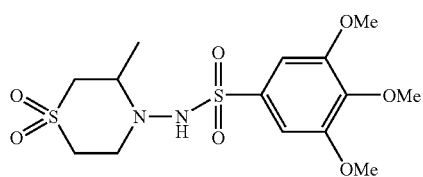

with the proposed systematic name N-(3-methyl-1,1-dioxo-1,4-thiazinan-4-yl)-1-[1-(3,4,5-trimethoxy phenyl sulfonyl]; and,

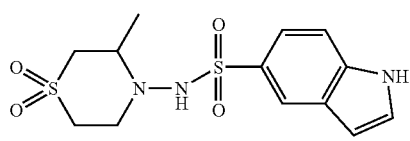

with the proposed systematic name N-(3-methyl-1,1-dioxo-1,4-thiazinan-4-yl)-1-(indole-5-sulfonyl].

The use of the compositions of this invention specifically contemplates treatment of neoplasms and cancers. Particular reference is made to neuroblastoma, ovarian, breast and colon cancer. Dosage ranges are determinable empirically by titrating up to a therapeutically effective dose. Note is also made of dosages of from about 0.005 mg to 5 g per day or as prescribed by the attending physicians. In some regimens, dosages are approximately 0.01 to 1000 milligram (mg) per kilogram (kg) of body weight of recipient per day, with specific reference to approximately 1 to 100 mg per kg of body weight of recipient per day. Further reference is made to dosage of about 2 to 20 mg per kg of body weight of recipient per day. In particular instances, treatment dosage regimens are daily or every other day for from about 2 weeks to one month or longer.

Compounds of Group I, II and IV are generally referred to as 4N-substituted N-amino tetrahydrothiazines.

Compounds of Group III are generally referred to as 4N-(substituted 1,4-thiazinan-4yl)-1-aryl methanimine Compounds of Group V are generally referred to as 4N-amido-N-amino tetrahydrothiazines.

Compounds of Group VI are generally referred to as 4N-sulfonamido-N-amino tetrahydrothiazines.

Methods of this invention include a hydrazine-free method of making a N-amino, 3-methyl tetrahydrothiazine-1,1-dioxide, Group IV, comprising the steps of (a) adding to a solution a sulfone of structure:

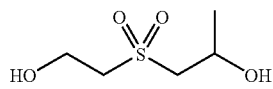

in concentrated aqueous sodium hydroxide, tent-Butyl carbazate, (b) mixing these components for approximately 1 to 24 hours at reflux, (c) cooling the reaction mixture to about 20 to 25° C. (room temperature), (d) extracting the mixture with ethyl acetate, drying the organic layer with anhydrous sodium sulfate (e) concentrating the organic layer under reduced pressure yielding

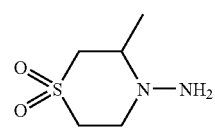

with the proposed systematic name N-amino, 3-methyl tetrahydrothiazine-1,1-dioxide.

Further included is a method of making a compound of Group I comprising the steps of:

(a) reacting N-amino, 3-methyl tetrahydrothiazine-1,1-dioxide (Group IV) with

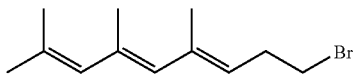

with the proposed systematic name 1-bromo, 4,6,8-trimethyl, nona-3,5-7-triene in dimethylformamide (DMF);

(b) adding to the reaction mixture potassium carbonate and heating to about 80-100° C. for about 8 hours;

(c) cooling the reaction mixture to about 20-25° C.;

(d) extracting this mixture with ethylacetate;

(e) concentrating and purifying the organic layer to yield a compound belonging to Group I

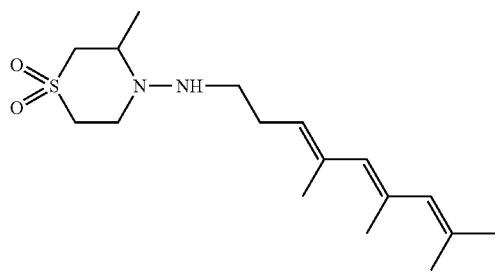

with the proposed systematic name (N-[amino(4,6,8-trimethyl, 3,5,7-nonatriene)-1-yl)], 3-methyl tetrahydrothiazine-1,1-dioxide) as shown below:

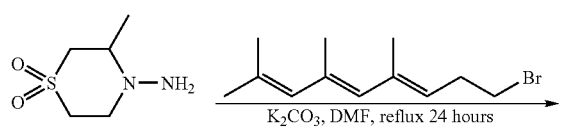

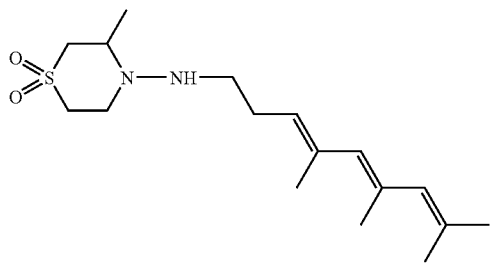

In another embodiment the invention includes a method of making a compound of Group II comprising the steps of (a) reacting N-amino, 3-methyl tetrahydrothiazine-1,1-dioxide (Group IV) with diphenylbromomethane in DMF;

(b) adding to the reaction mixture potassium carbonate and heating to about 80-100° C. for about 8 hours;

(c) cooling the reaction mixture to about 20-25° C.;

(d) extracting this mixture with ethylacetate;

(e) concentrating and purifying the organic layer to yield a compound belonging to Group II,

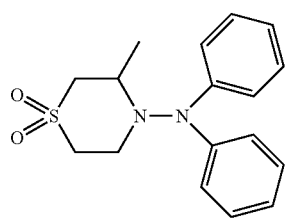

with the proposed systematic name (N-(diphenylamino),3-methyltetrahydrothiazine-1,1-dioxide) as shown below.

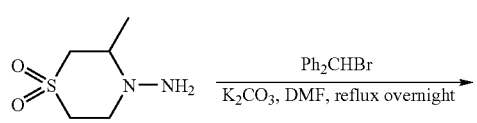

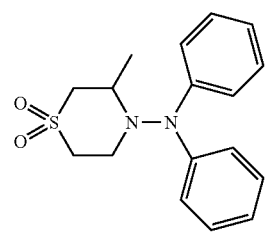

A specific method of the invention is a method of making a compound of Group III comprising the steps of:

(a) reacting N-amino, 3-methyl tetrahydrothiazine-1,1-dioxide (Group IV) with

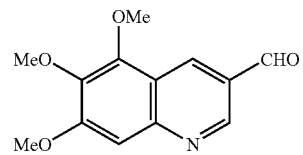

having a proposed systematic name 5,6,7-trimethoxyquinoline-3-carboxaldehyde in ethanol;

(b) refluxing the reaction mixture for about 1 to 24 hours;

(c) cooling the reaction mixture to about 20-25° C.;

(d) filtering the reaction mixture to yield a compound belonging to Group III,

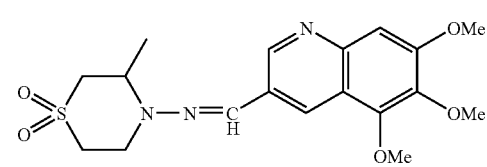

with a proposed systematic name (N-(3-methyl-1,1-dioxo-1,4-thiazinan-4-yl)-1-[4,5,6-trimethoxy quinoline-3-ly]methanimine) as shown below.

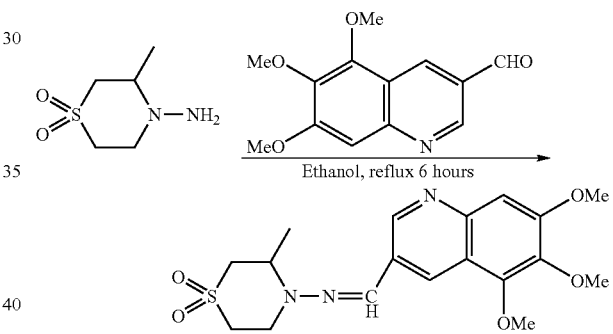

This invention includes a method of making a compound comprising the steps of:

(a) reacting N-amino, 3-methyl tetrahydrothiazine-1,1-dioxide (Group IV) with iodobenzene in DMF;

(b) adding to the reaction mixture potassium carbonate and heating to about 80-100° C. for about 8 hours;

(c) cooling the reaction mixture to about 20-25° C.;

(d) extracting this mixture with ethylacetate;

(e) concentrating and purifying the organic layer;

(f) reacting the product of the organic layer,

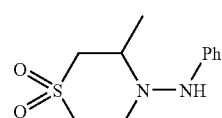
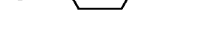

with the proposed systematic name (N-(phenylamino), 3-methyltetrahydrothiazine-1,1-dioxide), with 2-bromofuran, potassium carbonate, palliadium chloride and triphenylphosphine in DMF;

(g) heating to about 80-100° C. for about 2 days;

(h) cooling the reaction mixture to about 20-25° C.;

(i) extracting this mixture with ethylacetate;

(j) concentrating and purifying the organic layer to yield a compound belonging to Group IV,

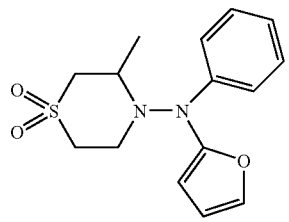

with the proposed systematic name (N-(3-methyl, 1,1-dioxo, thiomorpholino-4-yl)-N-(2-furylaniline)) as shown below.

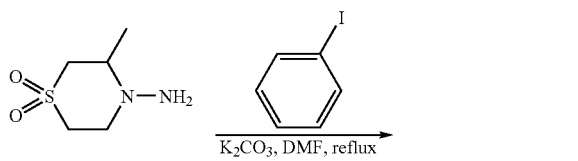

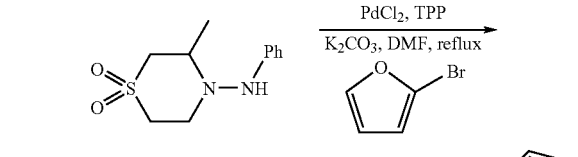

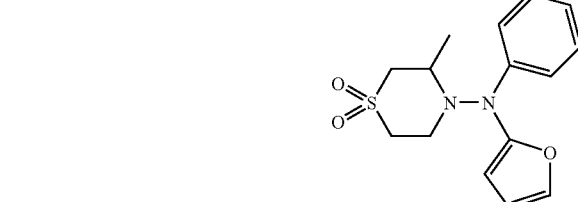

Attention is also drawn to a method of making a compound comprising the steps of (a) reacting N-amino, 3-methyl tetrahydrothiazine-1,1-dioxide (Group IV) with diphenylacetyl chloride in DMF;

(b) adding to the reaction mixture potassium carbonate and stirring for about 8 hours;

(c) extracting this mixture with ethylacetate;

(d) concentrating and purifying the organic layer to yield a compound belonging to Group V,

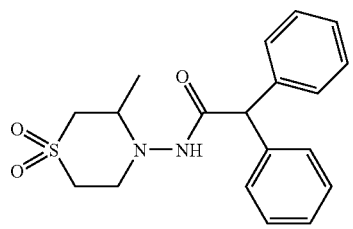

with the proposed systematic name (N-(diphenylacetamido), 3-methyl tetrahydrothiazine-1,1-dioxide) as shown below.

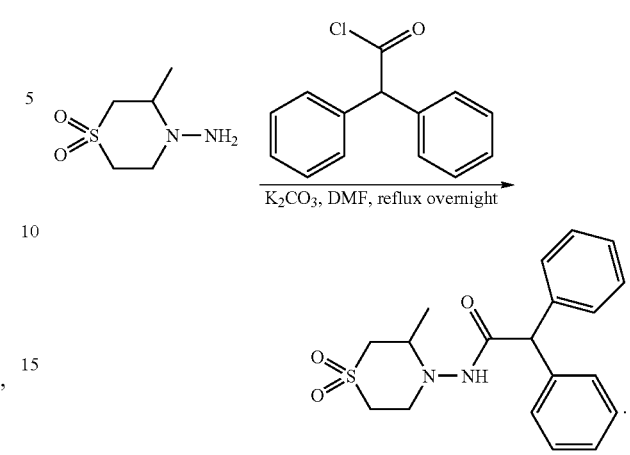

This invention includes a method of making a compound comprising the steps of (a) reacting N-amino, 3-methyl tetrahydrothiazine-1,1-dioxide (Group IV) with

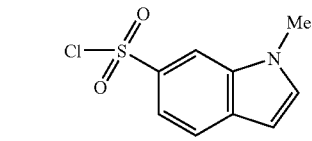

having a proposed systematic name 1-methyl indole-6 sulfonyl chloride in tetrahydrofuran;

(b) adding to the reaction mixture triethylamine and stirring for about 8 hours;

(c) extracting this mixture with ethylacetate;

(d) concentrating and purifying the organic layer to yield a representative compound belonging to Group VI,

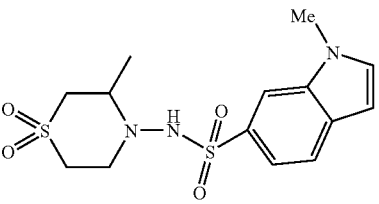

with a proposed systematic name (N-(1-methylindole, 6-sulfonamido), 3-methyltetrahydrothiazine—as shown below.

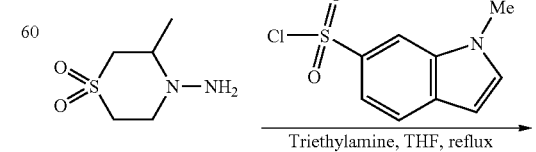

-continued

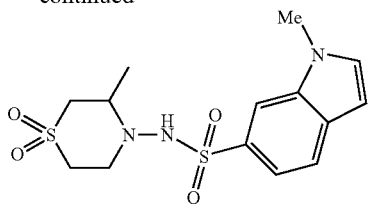

DETAILED DESCRIPTION OF THE INVENTION

Figure 1:
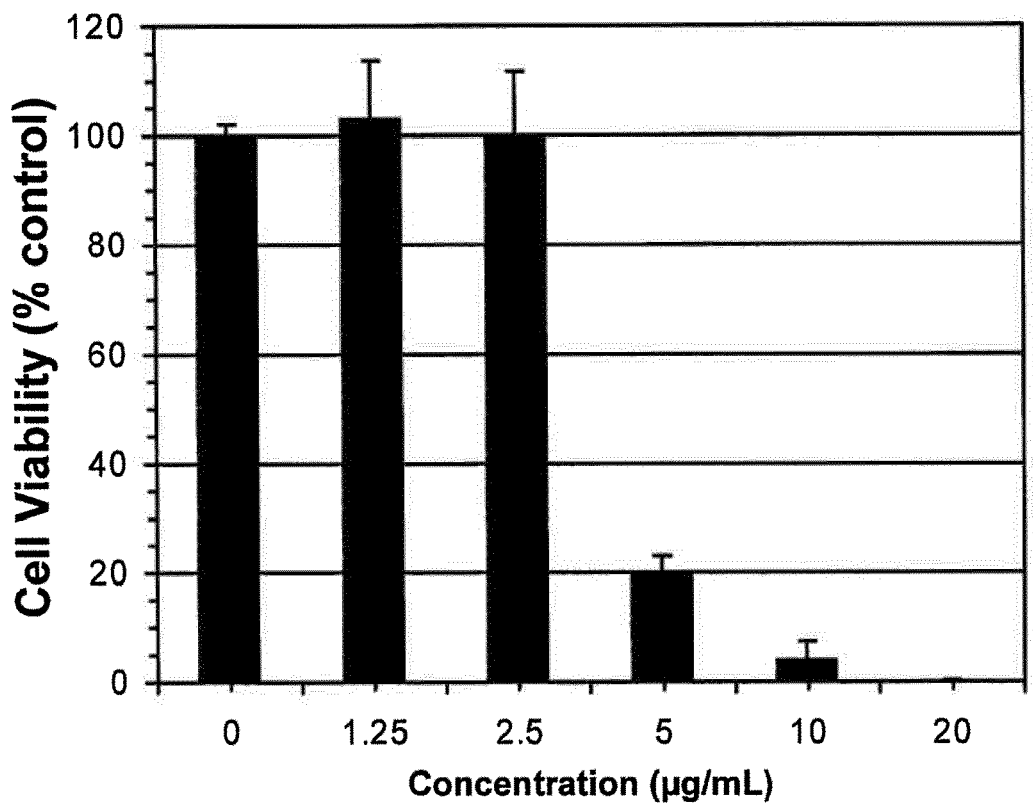
FIG. 1. is a graph of biological activity of an N-amino tetrahydrothiazine derivative against Neuroblastoma cells.

The invention will be better understood with reference to the following definitions:

A. The term "Alkyl" shall mean one or more linked carbon atoms such as $(C)_n$ such that "n" is any number of carbons in a chain. Contemplated chains include linear, branched or cyclic chains including alkene, alkenyl, alkynyl, with particular mention of carbon chains where n=2-20. This term is exemplified by groups such as methyl, ethyl, n-propyl, n-butyl, iso-butyl, tert-butyl, n-hexyl and n-decyl, tetradecyl, cyclohexyl, cyclopropyl and the like.

B. "Substituted/substituents" is used in conjunction with alkyl. Substituents(s) can be pendent from the alkyl group, interrupt the alkyl group, or be both pendent from and interrupting the alkyl group. Substituted alkyl moieties are also contemplated within the definition of alkyl. Substituted alkyls include, for example, alkenyl, alkynyl, alkoxy, cycloalkoxy, cycloalkenyl, ketone, acyl, acylamino, acyloxy, alkoxycarbonylamino, azido, cyano, halogen, hydroxyl, oxo, thiocarbonyl, carboxy, arythio, thiol, alkylthio, aryloxy, aralkoxy, heteroaryloxy, aminosulphonyl, COOR where R is defined as follows in C.

C. R is selected independently from hydrogen, alkyl, aryl, heteroaryl, alkyl aryl, arylalkyl, alkenyl, alkynyl, amino, hydroxyl, halogens, acids, amides, reverse amides, acyls, carbamates, ureas, or thioureas, esters, aldehydes, NHC(=O)$R^1$x, $NR^1xR^2x$, —NHC(=O)$NR^1xR^2x$, C(=O)aryl, C(=O)heteroaryl, C(=O) heterocyclylalkyaryl, C(=O)alkyl, —OC(=O) $NR^1xR^2x$, [where $R^1$ and $R^2$ are independently hydrogen, alkyl, aryl, aryl alkyl and x is independently integers 1 or 2], $NO_2$, sulphonyls and/or derivatives such as chloride, amides, sulphonic acids, phosphates and nitriles. The derivatives of acids such as hydroxamates, hydrazides are also included herein except as to formula III wherein the imine R group cannot be 2-nitrofuran. It is further contemplated that additional substituents may be constructed onto a basic organometallic complex with equivalent or improved activity. It is further contemplated that additional substituents may be constructed onto the basic organometallic complex with equivalent or improved activity.

D. The term "aryl" means $C_4$ to $C_{12}$ aromatic or heteroaromatic ring systems which further include ring substitution with alkyl groups and other functional groups such as —OH and derivatives thereof such as ethers, and acetates, NRR and derivatives thereof, such as amides, thioamides, ureas, thioureas, carbamates, thiocarbamates etc, SH and derivatives thereof such as thioethers, and COOH and derivatives thereof such as esters, amides.

Particular reference is made to the substitutions of the groups described above with the following classes of groups such as amino acids (optically active, including antipodes, racemic, and synthetic/unnatural amino acids), peptides (open or cyclic) containing all coded and uncoded amino acids (as described in the literature) in single or in multiple repeating units such as peptides or polypeptides. Sugars and other class of molecules, including natural product derivatives such as hormones, vitamins etc.

E. The term "alkylarene" is used herein to refer to a subset of "aryl" in which the aryl group is substituted with an alkyl group.

F. The term "ketone" is used to describe a ketone substituent, —C(=O)R, wherein R is described as above.

G. The term "alkoxy" is used herein to refer to the —OR group, wherein R is defined as above.

H. The term "aryloxy" refers to a group having the structure —O—Ar, where Ar is an aromatic group. Particular attention is drawn to the aryloxy group phenoxy.

I. The term "alkylamino" denotes secondary and tertiary amines wherein the alkyl groups may be either the same or different and may consist of straight or branched, saturated or unsaturated hydrocarbons.

J. The term "unsaturated cyclic hydrocarbon" is used to describe a non-aromatic group with at least one double bond, such as cyclopentene, cyclohexene, and substituted analogues thereof.

K. The term "heteroaryl" as used herein refers to aromatic rings in which one or more carbon atoms of the aromatic ring(s) are substituted by a heteroatom such as nitrogen, oxygen or sulfur. Heteroaryl structures may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, or benzo-fused analogues of these rings are included in the term "heteroaryl."

L. "Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are encompassed by the term "substituted heteroaryl."

M. "Alkylheteroaryl" defines a subset of "heteroaryl" substituted with an alkyl group.

N. The term "heterocyclic" is used herein to describe a saturated or unsaturated non-aromatic group having a single ring or multiple condensed rings from 1-12 carbon atoms and from 1-4 heteroatoms selected from nitrogen, sulfur or oxygen within the ring. Such heterocycles are, for example, tetrahydrofuran, morpholine, piperidine, pyrrolidine, etc.

O. The term "substituted heterocyclic" as used herein describes a subset of "heterocyclic" wherein the heterocyclic nucleus is substituted with one or more functional groups such as lower alkyl, ketones, acyl, halogen, alkylhalos (e.g. $CF_3$), hydroxy, amino, alkoxy, alkylamino, acylamino, acyloxy, mercapto, etc.

P. The term "alkylheterocyclyl" defines a subset of "heterocyclic" substituted with an alkyl group, as defined herein.

Q. The term "substituted heterocyclicalkyl" defines a subset of "heterocyclicalkyl" wherein the heterocyclic nucleus is substituted with one or more functional groups such as lower alkyl, ketones such as alkanones, aryl alkyl ketone, diaryl ketones, halogen, alkylhalos (e.g. $CF_3$), hydroxy, amino, alkoxy, alkylamino, acylamino, acyloxy, mercapto, etc.

R. The term "fatty acid ester," as used herein, refers to a substituent that is derived from a fatty acid by removal of hydrogen. When present, the fatty acid esters typically occupy no more than two substituent positions and are usually identical.

An improved, more efficient and less hazardous synthesis of N-amino, 3-methyl tetrahydrothiazine-1,1-dioxide (Group IV) is herein presented. Prior published synthesis of N-amino, 3-methyl tetrahydrothiazine-1,1-dioxide and its analogs and derivative were tedious, and required the use of large quantities of highly carcinogenic, toxic, and explosive chemicals such as hydrazine. Hence a cleaner, environmentally friendly, and efficient method has now been devised. This method involves the replacement of hydrazine with tert-Butyl carbazate, a solid which is easier and safer to handle. A further improvement is that the N-tert-butoxycarbonyl (t-BOC) protection of one of the amino groups of tert-Butyl carbazate was conveniently reversed under the disclosed cyclization conditions (concentrated aqueous sodium hydroxide at reflux for 1-24 hours). Development of such an efficient, convenient, and non-toxic one-step cyclization and simultaneous t-BOC deprotection represents advancement in the synthesis of these compounds.

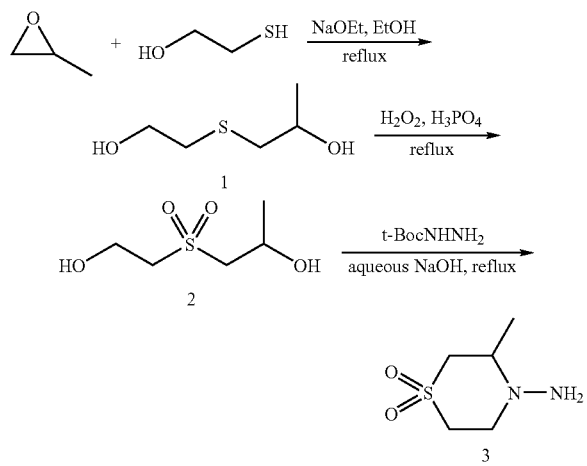

N-amino tetrahydrothiazine derivative (5, Group III) was synthesized following the scheme below.

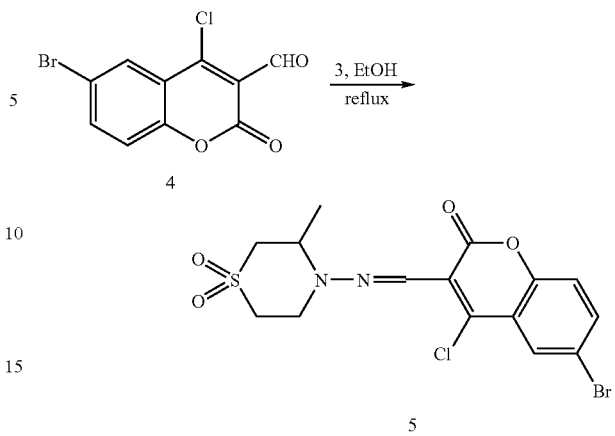

The synthesis of diol (1) was achieved with a base promoted nucleophilic addition of mercaptoethanol to propylene oxide at reflux in ethanol. This reaction is achievable with other solvents including (beyond ethanol), THF, diethyl ether, DMSO, NMP, DMF and with bases such as sodium ethoxide, sodium hydride, sodium methoxide and the like. All reagent, solvent, and reaction conditions such as temperature, time and workup and purification protocol and their combinations to achieve the synthesis are contemplated within the purview of this invention. Diol (1) was characterized by $^1$HNMR and Mass spectrometry.

$^1$H NMR (CDCl$_3$): δ 3.868 (1H), 3.734 (2H), 2.725 (4H), 2.465 (2H), 1.222 (3H)

MS (FAB): 159 [M+Na]$^+$

The synthesis of sulfone diol (2) was achieved with hydrogen peroxide solution with catalytic amounts of acids such as phosphoric acid, at reflux over a period of 24 hrs. The solvent was removed under reduced pressure or under stream of air, $N_2$ or argon and then dried under high vacuum. Diol (2) was characterized by $^1$HNMR and Mass spectrometry $^1$H NMR(CDCl$_3$): δ 4.48 (1H), 4.12 (2H), 3.31 (3H), 3.13 (1H), 1.31 (3H); MS (FAB):191 [M+Na]$^+$.

The cyclization of sulfone diol (2) to N-amino tetrahydrothiazine derivative (Group IV) (3) was achieved as follows. To a solution of sufone diol 2 (1 eq.) in concentrated aqueous sodium hydroxide solution was added tBoc-NHNH$_2$ (tent-Butyl carbazate, 1.25 eq.). The reaction mixture was refluxed and the progress of reaction monitored by thin layer chromatography (TLC). After completion of the reaction (approximately 24 hours), the reaction mixture was allowed to cool to room temperature (about 20-25° C.) and extracted with ethyl acetate. The organic was dried over anhydrous sodium sulfate and concentrated under reduced pressure to afford intermediate 3 as a viscous oil, which solidified partially when placed in a refrigerator (at 0-5° C.) over a period of time. The compound was characterized by mass spectrometry. MS (FAB): 165.2 [M+H]$^-$, 187 [M+Na]$^+$.

The synthesis of N-amino tetrahydrothiazine derivative (5, Group III, RKS-2-62) was achieved by condensation of N-amino tetrahydrothiazine derivative (3) (1.1 eq.) with the corresponding coumarine-3-carboxaldehyde 4 (1 eq.) at reflux for up to 24 hours, in alcoholic solvents such as ethyl alcohol, particularly anhydrous. Of note, this condensation reaction can also be achieved using various other conditions, such as other solvents, varying the temperature, changing time of reaction, and/or using catalysts. Furthermore, methods which create an imine bond between an aldehyde or ketone and an amine functionality, yielding compounds from Group III are included in this invention. Particular reference is made to reflux of solvent or solvent mixtures including ethanol and water. Finally, the reaction mixture was filtered at room temperature under suction to afford the desired product.

¹H NMR (DMSO-d6): δ 8.05 (1H), 7.82-8.04 (1H), 6.69 (1H), 7.43-7.46 (1H), 4.45 (1H), 3.38-3.99 (2H), 2.82-3.24 (4H) and 1.05-1.07(d, 3H).

Without limitation, particular note is made of the following Group I-II compounds

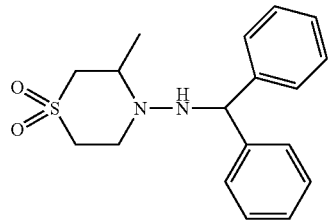

N-(3-Methyl-1,1-dioxo-1,4-thiazinan-4-yl)-1-[1,1-diphenyl] methane

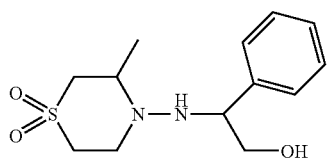

N-(3-Methyl-1,1-dioxo-1,4-thiazinan-4-yl)-1-[1-phenyl,1-methanol] methane

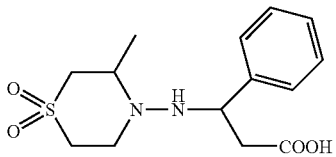

N-(3-Methyl-1,1-dioxo-1,4-thiazinan-4-yl)-1-[1-phenyl, 1-acetic acid] methane

Without limitation, particular note is made of the following Group III compounds:

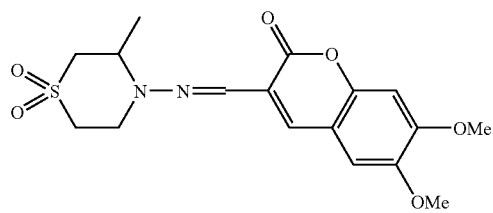

N-(3-Methyl-1,1-dioxo-1,4-thiazinan-4-yl)-1-[5,6-dimethoxy coumarin-2-yl] methanimine

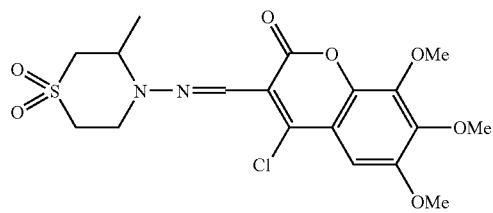

N-(3-Methyl-1,1-dioxo-1,4-thiazinan-4-yl)-1-[3-chloro, 5,6,7-trimethoxy coumarin-2-yl] methanimine

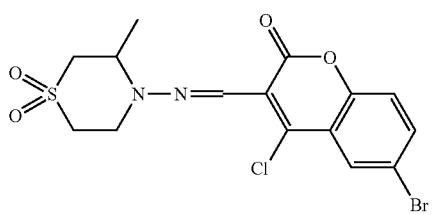

N-(3-Methyl-1,1-dioxo-1,4-thiazinan-4-yl)-1-[3-chloro, 5-bromo coumarin-2-yl] methanimine The Pictured compound, N-(3-Methyl-1,1-dioxo-1,4-thiazine-4-yl)-1-[3-chloro, 5-bromo coumarin-2-yl]methanimine is also termed RKS-2-62.

Without limitation, particular note is made of the following Group IV compounds:

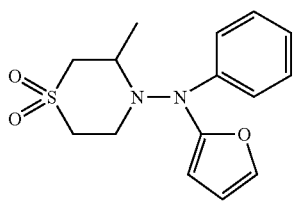

N-(3-Methyl-1,1-dioxo-1,4-thiazinan-4-yl)-1-[1-phenyl, 1-furan-2-yl]

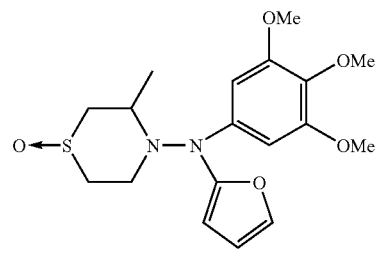

N-(3-Methyl-1-oxo-1,4-thiazinan-4-yl)-1-[1-(3,4,5-trimethoxy phenyl), 1-furan-2-yl]

Without limitation, particular note is made of the following Group V compounds:

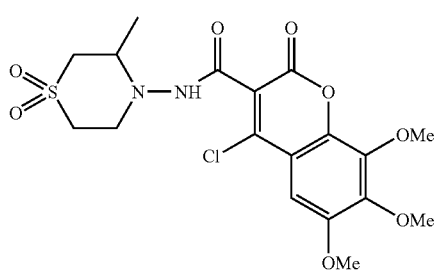

N-(3-Methyl-1,1-dioxo-1,4-thiazinan-4-yl)-1-[3-chloro,5,6,7-trimethoxy courmarin-2-carbonyl]

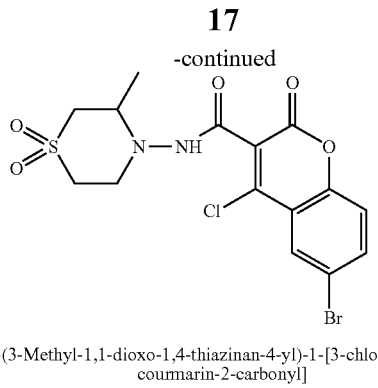

N-(3-Methyl-1,1-dioxo-1,4-thiazinan-4-yl)-1-[3-chloro,5-bromo coumarin-2-carbonyl]

Without limitation, particular note is made of the following Group VI compounds:

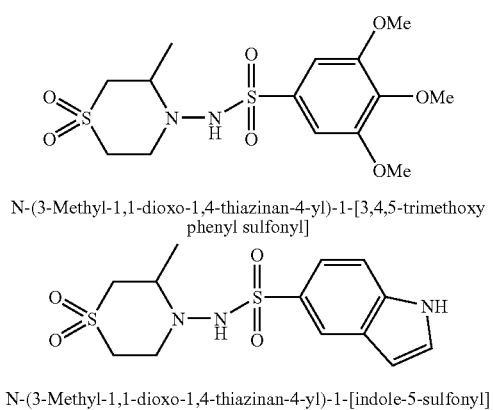

N-(3-Methyl-1,1-dioxo-1,4-thiazinan-4-yl)-1-[3,4,5-trimethoxy phenyl sulfonyl]

N-(3-Methyl-1,1-dioxo-1,4-thiazinan-4-yl)-1-[indole-5-sulfonyl]

Studies indicate that RKS-2-62 is effective in decreasing viability of neuroblastoma cells. Indications suggest that it is more effective than nifurtimox. Data show that RKS-2-62 is more effective than nifurtimox in decreasing viability of medulloblastoma cells.

In addition, RKS-2-26 is lipid soluble and likely to cross the blood brain barrier. RKS-2-62 solution of 10 μg/μL was shown to dissolve in chloroform. Then 1 mL of distilled water was added and vortexed. The RKS-2-62 remained solely in the chloroform layer and not the aqueous layer suggesting that this compound will likely cross the blood brain barrier and therefore be able to reach medulloblastoma tumors.

Example 1

RKS-2-62 in Neuroblastoma

Figure 2:
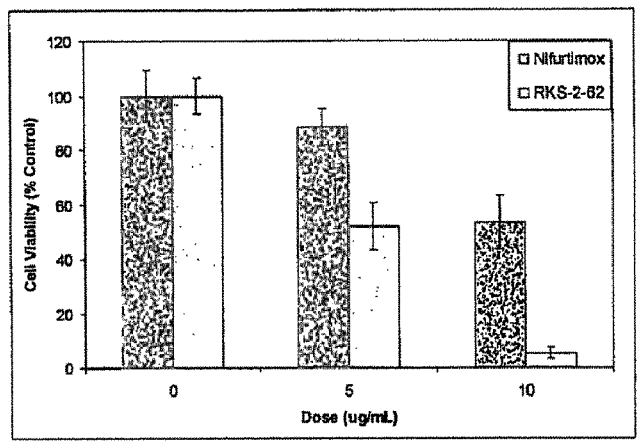
FIG. 2. is a graph of RKS-2-62 and nifurtimox against neuroblastoma cells.

SMS-KCNR neuroblastoma cells were incubated for 48 hours with increasing levels of either nifurtimox or RKS-2-62, and cytotoxicity was determined using the Calcein AM cell viability assay. RKS-2-62 inhibited the growth of these cell lines in a dose-dependent manner and to a greater extent than nifurtimox After 48 hours of exposure to only 5 μg/mL the mean value for RKS (51.9%+/−8.4%) was significantly lower than for Nftx (88.4%+/−6.8%) using a two sample t-test (P<0.001). FIG. 2 is a graph of RKS-2-62 and nifurtimox against neuroblastoma cells. RKS-2-62 is cytotoxic to neuroblastoma cells in vitro. SMSKCNR cells were plated in 48 wells plates and treated with 0-20 μg/mL of either RKS-2-62 or nifurtimox for 48 hours. Cell viability was assessed using Calcein AM assay.

Example 2

RKS-2-62 in Medulloblastoma

Figure 3:
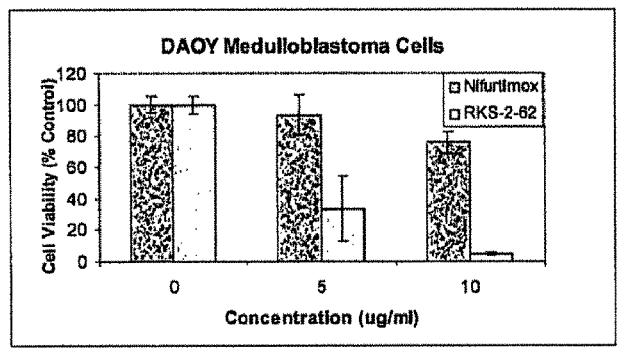
FIG. 3 is a graph of RKS-2-62 and nifurtimox against DAOY medulloblastoma cells.
Figure 3A:
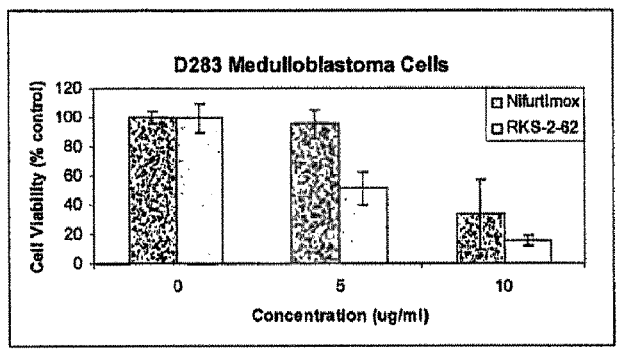
FIG. 3a is a graph of RKS-2-62 and nifurtimox against D283 medulloblastoma cells.

The medulloblastoma cell lines DAOY (FIGS. 3) and D283 (FIG. 3a) were incubated for 48 hours with increasing doses of nifurtimox or RKS-2-62, and cytotoxicity was determined using the Calcein AM cell viability assay. DOAY and D283 cells were plated in 48 wells plates and treated with 0-10 μg/mL of either RKS-2-62 or nifurtimox for 48 hours. RKS-2-62 inhibited the growth of both cell lines in a dose-dependent fashion and to a greater extent than nifurtimox. As shown in FIGS. 3 and 3a, exposure to 10 μg/mL of RKS-2-62 for 48 hours decreased viability of both cell lines by over 80%. For the D283 cell line, viability after exposure to RKS was decreased compared to nifurtimox (P=0.008), with similar results for the DAOY cell line (P=0.026).

Example 3

RKS-2-62 in Neuroblastoma

Figure 4:
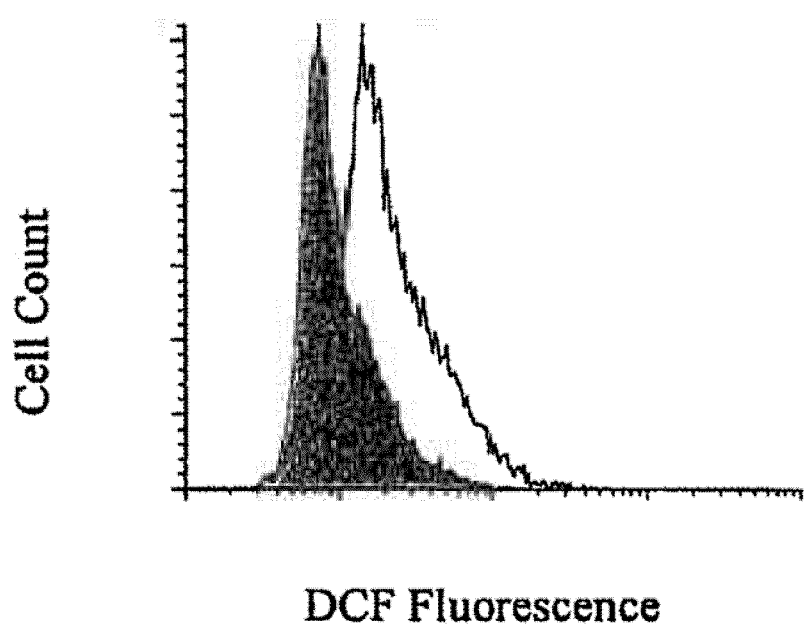
FIG. 4 is a graph of RKS-2-62 increasing reactive oxygen species in neuroblastoma cells.

RKS-2-62 increases reactive oxygen species in neuroblastoma cells. SMSKCNR cells treated with RKS-2-62 were incubated with carboxyl-DCF. SMSKCNR cells were grown in T25 flasks and incubated in RKS-2-62 for 90 minutes prior to treatment with carboxylated DCF. Cells were collected and analyzed by flow cytometry. As shown in FIG. 4, an increase in production of ROS in response to RKS-2-62 was seen. Control is the left hand peak in grey. RKS-2-62 is the right hand peak. Oxidation of DCF by reactive oxygen species (ROS) causes increased fluorescence, and a lower concentration of RKS-2-62 than of nifurtimox was required to achieve the same effect.

Example 4

Oral RKS-2-62 in Neuroblastoma

Figure 5:
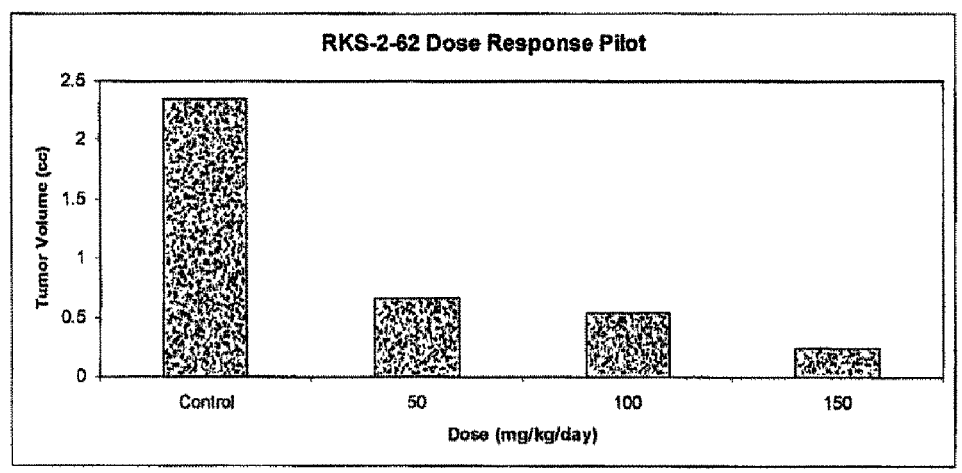
FIG. 5 is a graph of a xenograft mouse model showing a decrease in tumor growth at all dose levels when treated with RKS-2-62.

Oral RKS-2-62 inhibits neuroblastoma growth in vivo. A xenograft mouse model showed a decrease in tumor growth at all dose levels when treated with RKS-2-62. Nude mice were injected subcutaneously in the flank with $10^7$ SMSKCNR cells and tumors were allowed to grow for 7 days. Mice were then fed either control food pellets or pellets containing 50, 100, or 150 mg/kg/day of RKS-2-62 for 3 weeks (4 mice per group). Tumors were harvested and weighed. Average weights are shown in FIG. 5. At all three dosing levels, tumor weight was decreased by greater than 75% compared to the control group. RKS-2-62 was better tolerated in mice than nifurtimox, with no weight loss or ataxia noted even at the highest dose level. Fisher's LSD pairwise mean comparisons indicate that each of the three dose levels have significantly smaller tumor volumes compared to control (each p<=0.002). However, the differences in volumes between the 50, 100 and 150 mg/kg/day dose levels were not statistically significant.

Example 5

Treatment of Neuroblastoma

A 30 month old male presents with Stage IV neuroblastoma. The infant is treated 15 mg/kg/day dose of N-(3-methyl-1,1-dioxo-1,4-thiazinan-4-yl)-1-[1,1-diphenyl]methane orally or intravenously ("IV") for 2 weeks and shows tumor stabilization with increased quality of life. With the further addition of cyclophosphamide and topotecan the patient shows significant and continuous tumor regression for 8 weeks. Upon examination, tumor mass is found reduced by about 50%.

Example 6

Treatment of Breast Cancer

A 30 year old female subject presents with Stage IV breast cancer and axillary lymph node involvement. The subject is treated with 10 mg/kg/day of N-(3-methyl-1,1-dioxo-1,4-thiazinan-4-yl)-1-[1-phenyl, 1-methanol]methane orally or IV daily for 15 consecutive days. Upon examination, cancer involvement is found reduced by about 20%.

Example 7

Treatment of Pancreatic Cancer

A 53 year old male subject presents with Stage IV pancreatic cancer. The subject is treated daily with 10 mg/kg/day of N-(3-methyl-1,1-dioxo-1,4-thiazinan-4-yl)-1-[1-phenyl, 1-acetic acid]methane by tablets every other day for 30 consecutive days (15 doses). Upon examination, cancer involvement is found reduced by about 20%.

Example 8

Breast Cancer Prophylaxis

A 39 year old female subject presents normally, but has BRCA 1 and 2 markers as well as a family history of breast cancer. The subject is treated daily with 5 mg/kg of N-(3-methyl-1,1-dioxo-1,4-thiazinan-4-yl)-1-[5,6-dimethoxy coumarin-2-yl]methanimine by tablets for 48 months. Upon examination, no cancer involvement is found.

Example 9

Liver Cancer Treatment

A 66 year old male subject presents with end stage liver cancer refractory to all other treatments. The subject is treated daily with 10 mg/kg of N-(3-methyl-1,1-dioxo-1,4-thiazinan-4-yl)-1-[1-phenyl, 1-furan-2-yl] orally or IV for 48 days. Upon examination, no liver cancer involvement is found.

Example 10

Ovarian Cancer Treatment

A 56 year old female subject presents with recurrent/progressive stage III ovarian cancer refractory to all other treatments. The subject is treated daily with 10 mg/kg of N-(3-methyl-1,1-dioxo-1,4-thiazinan-4-yl)-1-[3-chloro, 5-bromo coumarin-2-carbonyl] orally or IV for 48 days. Upon examination, no further tumor growth is noted.

Example 10

Alzheimer Treatment

A 79 year old female subject presents with Stage V Alzheimer's disease. The subject is treated daily with 5 mg/kg oral doses of N-(3-methyl-1,1-dioxo-1,4-thiazinan-4-yl)-1-[3,4, 5-trimethoxy phenyl sulfonyl], chronically. Upon examination over a six month period, substantially no progression of the disease is noted.

According to this invention, a therapeutically or pharmaceutically effective amount of N-amino tetrahydrothiazine derivatives is administered to subjects (with particular reference to mammals, and more particular reference to humans) to treat or prevent neoplastic disease with particular reference to cancer. In particular embodiments the N-amino tetrahydrothiazine derivatives of this invention therapeutically treat neuroblastoma, pancreatic, ovarian, prostate, endometrial, cervical and colorectal cancers as well as lymphoma and leukemia.

A therapeutically effective dose will depend upon the nature of the disease, the severity and course of the disease, previous therapy, the patient's health status, response to the N-amino tetrahydrothiazine derivatives and the judgment of the treating medical caregiver. Typically, at least one N-amino tetrahydrothiazine derivatives is administered as a sole active ingredient, or in combination with one or more other active ingredients. Typically co-administered drugs are N-2-mercaptopropionylglycine, N-acetylcysteine, glutathione, dimethyl thiourea, desferrioxamine, mannitol, α-tocopherol, ascorbate, buthionine sulfoximine, allopurinol, 21-aminosteroids, calpain inhibitors, glutamate receptor antagonists, tissue plasminogen activator, streptokinase, urokinase, non-steroidal anti-inflammatory agent, cortisone, and carotenoids. N-amino tetrahydrothiazine derivatives are also administered in conjunction with polypeptides having SOD and/or catalase activity.

The present invention includes a method of treating patients who have a neoplasticity associated disease with a prophylactically effective or therapeutically effective amount of a N-amino tetrahydrothiazine derivative. This method is useful to treat patients at various stages of their diseases or to prevent development of such diseases. In addition, the treatment can be administered to prevent or reduce the incidence of developing a neoplasm.

The N-amino tetrahydrothiazine derivatives of the invention are also usefully administered to patients who are infected with a human immunodeficiency virus (e.g., HIV-1) or who are at risk of becoming infected with a human immunodeficiency virus. The N-amino tetrahydrothiazine derivatives prevent or inhibit the induction of HIV-1 replication in CD4+ lymphocytes. Without being bound by any particular theory, this effect is achieved by acting on or interfering with tumor necrosis factor (TNF) and/or preventing damage to or death of CD4+ cells as a consequence of HIV-1 infection. Again, without wishing to be bound by any particular theory of HIV-1 replication or HIV-1 pathogenesis, it is believed that administration of N-amino tetrahydrothiazine derivatives inhibits development of HIV-1 related pathology and/or reduces the rate of decline of the CD4+ lymphocyte population in HIV-infected individuals. The N-amino tetrahydrothiazine derivatives also inhibit pathology resulting from excessive or inappropriate levels of TNF, both in AIDS and in other conditions associated with TNF elaboration (e.g., septic shock). In some instances, a dosage of about 5 to 5000 mg will be administered to a patient with HIV and/or with excessive or inappropriate levels of TNF, either in single or multiple doses. N-amino tetrahydrothiazine derivatives are also usefully administered therapeutically to treat viral diseases other than HIV.

In general, for treatment of neoplastic diseases, a therapeutically effective dose of N-amino tetrahydrothiazine derivatives will be in the range of about 0.1 to 100 milligram (mg) per kilogram (kg) of body weight of recipient per day, and particularly in the range of about 1 to 20 mg per kg of body weight per day. The desired dosage is usefully presented in one, two, three, four or more subdoses administered at appropriate intervals throughout the day. These subdoses are administered as unit dosage forms, for example, containing about 5 to 10,000 mg, and particularly about 10 to 2000 mg of N-amino tetrahydrothiazine derivatives per unit dosage form.

The composition used in these therapies can be in a variety of forms. These include, for example, solid, semi-solid and liquid dosage forms, such as tablets, pills, powders, liquid solutions or suspensions, liposome preparations, injectable and infusible solutions. The preferred form depends on the intended mode of administration and therapeutic application. Typically, a sterile solution of N-amino tetrahydrothiazine derivatives in an aqueous solvent (e.g., saline) will be administered intravenously. The contemplated compositions also include pharmaceutically acceptable carriers and adjuvants which are known to those of skill in the art. See, e.g., *Remington: The Science and Practice of Pharmacy*, Ed. Randy Hendrickson, Lippincott, Williams & Wilkins, 21$^{st}$ Edition (2005). Generally, administration will be by oral or parenteral (including subcutaneous, intramuscular, intravenous, and intradermal) routes, or by topical application or infusion into a body cavity, or as a bathing solution for tissues during surgery.

It should, of course, be understood that the methods of this invention are usefully employed in combination with antioxidant agents that have SOD (superoxide dismutase) activity, catalase activity, glutathione peroxidase (GSH-Px)) activity, or are free radical scavengers or inhibitors of free radical formation. It is possible to administer the active ingredient of this invention as a single active pharmaceutical agent, and also as part of a pharmaceutical formulation. The pharmaceutically acceptable formulations of the present invention comprise at least one compound of this invention in a therapeutically or pharmaceutically effective dose together with, optionally, one or more pharmaceutically or therapeutically acceptable carriers and optionally other therapeutic ingredients. Carriers include inert, non-toxic solids (e.g., mannitol, talc) and buffered saline. Various considerations are described in, for example, *Goodman and Gilman's: The Pharmacological Bases of Therapeutics*, Eds. Laurence Brunton, John Lazo, Keith Parker 11th Ed., Pergamon Press (2005); and Remington's supra, each of which is hereby incorporated herein by reference. Methods for administration are discussed therein, e.g., for oral, intravenous, intraperitoneal, or intramuscular administration, and others. Pharmaceutically acceptable carriers will include water, saline, buffers, and other compounds described in a number of sources including the *Merck Index*, Merck & Co., Rahway, N. J., incorporated herein by reference. As used herein, the term "pharmaceutically acceptable carrier" encompasses any of the standard pharmaceutical carriers such as sterile solutions, tablets, coated tablets, and capsules. Typically such carriers contain excipients such as starch, milk, sugar, certain types of clay, gelatin, stearic acids or salts thereof, magnesium or calcium sterate, talc, vegetable fats or oils, gums, glycols, or other known excipients. Such carriers may also include flavor and color additives or other ingredients. Compositions comprising such carriers are formulated by well known conventional methods.

Depending on the intended mode of administration and the intended use, the compositions may be in the form of solid, semi-solid, or liquid dosage forms, such as, for example, powders, granules, crystals, liquids, suspensions, liposomes, pastes, creams, salves, etc., and may be in unit-dosage forms suitable for administration of relatively precise dosages. For semi-solid compositions, as would be appropriate for pastes and creams intended for topical administration, the N-amino tetrahydrothiazine derivatives are provided separately or may be compounded with conventional nontoxic carriers such as, for example, aloe vera gel, squalane, glycerol sterate, polyethylene glycol, cetyl alcohol, stearic acid, and propylene glycol, among others. Such compositions may contain about 0.005-100% active ingredient, more particularly about 0.5-25%. The concentration of N-amino tetrahydrothiazine derivatives in these formulations varies widely. Selection of a specific concentration may consider intended use, viscosities, etc., in accordance with the particular mode of administration selected. Typical compositions include lotions containing water and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients are formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers.

The pharmaceutical compositions will be administered by parenteral or oral administration for prophylactic and/or therapeutic treatment. The pharmaceutical compositions can be administered in a variety of unit dosage forms depending upon the method of administration. For example, unit dosage forms suitable for oral administration include powder, tablets, pills, capsules, trochees, and dragees.

The pharmaceutical compositions will often be administered intravenously. Thus, this invention provides compositions for intravenous administration which comprise a solution of the compound dissolved or suspended in an acceptable carrier, with specific reference to an aqueous carrier. A variety of aqueous carriers can be used, e.g., water, buffered water, 0.4% saline, and the like. Often, the N-amino tetrahydrothiazine derivatives is dissolved in an organic solvent (e.g., dimethylsulfoxide) and either applied directly or diluted into an aqueous solvent. Typically, N-amino tetrahydrothiazine derivatives that are relatively lipophilic (e.g., C9, C12 and greater than C12) are dissolved in an organic solvent such as DMSO and, if desired, subsequently diluted into a more polar solvent, such as water. These compositions will sometimes be sterilized by conventional, well known sterilization techniques, or sterile filtered. The resulting aqueous solutions can be packaged for use as is, or lyophilized, the lyophilized preparation being combined with a sterile aqueous solution prior to administration. The compositions usefully contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.001-95% of active ingredient, with particular reference to about 20%.

The compositions containing the compounds are usefully administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective amount or dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

For solid compositions, conventional non-toxic solid excipients include, for example, pharmaceutical grades of mannitol, lactose, starch, magnesium stearate, talcum, celluloses, glucose, sucrose, magnesium carbonate, and the like may be used. The active compound as defined above may be formulated as suppositories using, for example, triglycerides, for example, any pharmaceutically acceptable Hard Fat NF bases (e.g., WITEPSOL.®™, Condea Vista Company, Cranford, N.J.), as the carrier. Liquid pharmaceutically administerable compositions can, for example, be prepared by dissolving, dispersing, etc. an active compound as defined above and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of inert auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington: The Science and Practice of Pharmacy*, Ed. Randy Hendrickson, Lippincott, Williams & Wilkins, 21$^{st}$ Edition (2005). The composition or formulation to be administered will, in any event, contain an effective amount of the active compound(s).

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of inert auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. Nos. 5,629,008, 5,851,547, 6,183,461, and 3,710,795, which are incorporated herein by reference. N-amino tetrahydrothiazine derivatives may be administered by transdermal patch (e.g., iontophoretic transfer) for local or systemic application.

Once detectable improvement of the patient's conditions has occurred, a maintenance dose is administered if necessary. Subsequently, the dosage or the frequency of administration, or both, is reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms or as a prophylactic measure to prevent disease symptom recurrence. In particular embodiments extended release formulations are contemplated.

N-amino tetrahydrothiazine derivatives are also be added to extravasated blood for transfusion to inhibit oxyradical damage to the blood cells and components during storage; similarly, N-amino tetrahydrothiazine derivatives reduce oxyradical damage to blood cells in vivo.

N-amino tetrahydrothiazine derivatives are usefully added to rinse or storage solutions for organs and tissues, such as for organ transplantation or for surgical rinses. For example, excised organs are often placed in a preservation solution prior to transplant into a recipient. Inclusion of at least one N-amino tetrahydrothiazine derivatives in a preservation solution, usually at a concentration of about 0.01 mM to 10 mM, is useful for reducing damage due to ischemia during storage and reperfusion injury following reimplantation in the recipient.

Typically a N-amino tetrahydrothiazine derivatives is present in the rinse or storage solution at a concentration of about 10 μM to about 10 mM, and most usually is present at 1 mM. For example, but not to limit the invention, a suitable rinse solution comprises Ringer's solution (102 mM NaCl, 4 mM KCl, 3 mM CaCl$_2$, 28 mM sodium lactate, pH 7.0) or Ringer's solution with 0.1 mM adenosine, and the N-amino tetrahydrothiazine derivatives at a final concentration of 1 mM. The rinse solution can further comprise additional antioxidants (e.g., glutathione, allopurinol). Preservation or rinse solutions containing a N-amino tetrahydrothiazine derivatives is used to provide enhanced storage or irrigation of organs (e.g., kidney, liver, pancreas, lung, fetal neural tissue, heart, vascular grafts, bone, ligament, tendon, skin) which is believed to enhance the viability of the tissue and increase resistance to oxidative damage (e.g., as a consequence of ischemia/reperfusion).

The invention claimed is:

1. A compound selected from the group consisting of

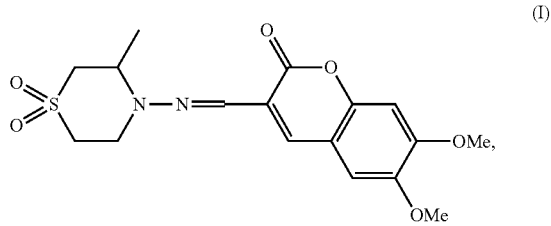

(I)

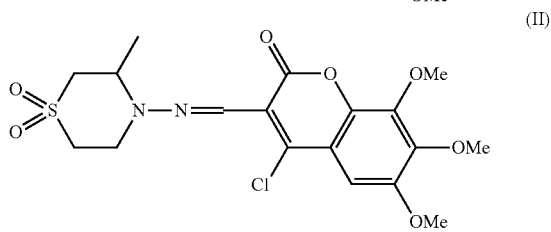

(II)

-continued

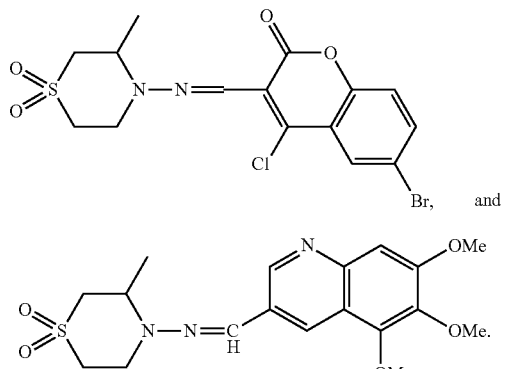

2. The compound of claim 1, which is

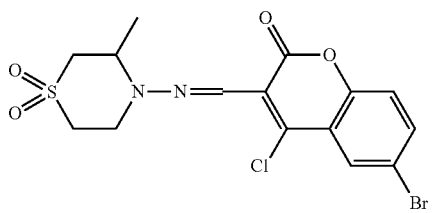

with the proposed systematic name N-(3-methyl-1,1-dioxo-1,4-thiazinan-4-yl)-1-{3-chloro,5-bromo coumarin-2-ly]methanimine, also named RKS-2-63.

3. A pharmaceutical composition comprising a therapeutically effective dose of a compound of claim 1 in a pharmaceutically acceptable carrier.

4. A pharmaceutical composition comprising a therapeutically effective dose of a compound of claim 2 in a pharmaceutically acceptable carrier.

5. The composition according to claim 3 wherein the dosage is from about 0.005 mg to 5 g per day.

6. The composition according to claim 4 wherein the dosage is from about 0.005 mg to 5 g per day.

7. The composition according to claim 3 wherein the dosage is from about 0.5 mg to 2 g per day.

8. The composition according to claim 4 wherein the dosage is from about 0.5 mg to 2 g per day.

9. The composition according to claim 3 wherein the dosage is from about 0.01 to 1000 mg per kilogram of body weight of recipient per day.

10. The composition according to claim 4 wherein the dosage is from about 0.01 to 1000 mg per kilogram of body weight of recipient per day.

11. The composition according to claim 3 wherein the dosage is from about 1 to 100 mg per kilogram of body weight of recipient per day.

12. The composition according to claim 4 wherein the dosage is from about 1 to 100 mg per kilogram of body weight of recipient per day.

13. The composition according to claim 3 wherein the dosage is from about 2 to 20 mg per kilogram of body weight of recipient per day.

14. The composition according to claim 4 wherein the dosage is from about 2 to 20 mg per kilogram of body weight of recipient per day.

15. A method of making the compound of formula (III) of claim 1 by the scheme below:

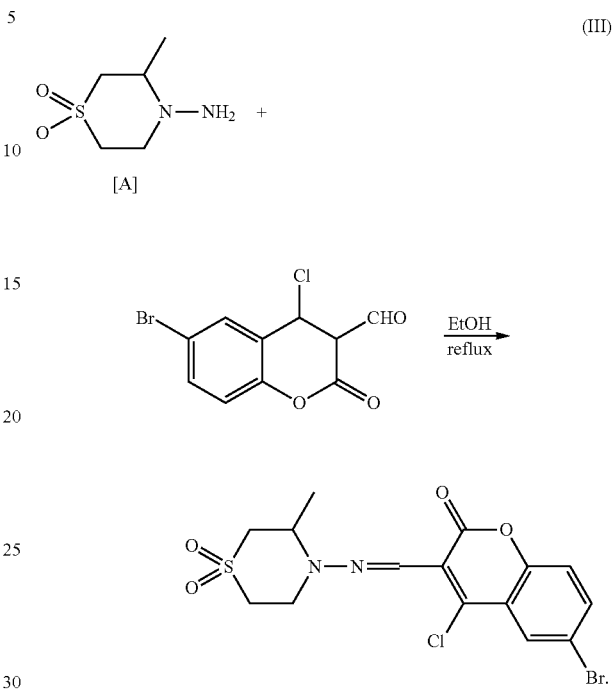

16. A method of making the compound of formula (IV) of claim 1 comprising the steps of (a) reacting N-amino,3-methyl tetrahydrothiazine-1,1-dioxide with

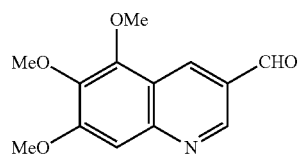

in ethanol;

(b) refluxing the reaction mixture;

(c) extracting the organic layer from the mixture yielding a compound of the following formula:

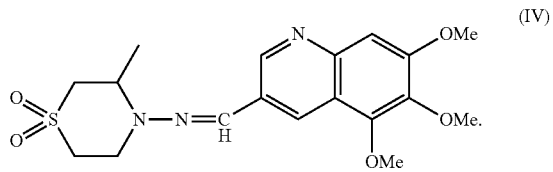

17. The method of claim 15 including making the starting material N-amino,3-methyl tetrahydrothiazine-1,1-dioxide (compound A) by the steps of (a) adding t-butyl carbazate to a solution of a sulfone of structure:

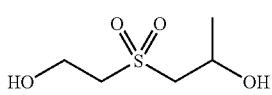

in aqueous sodium hydroxide;

(b) mixing these components at reflux;

(c) extracting the organic layer from the mixture yielding

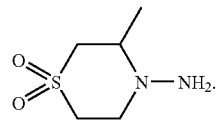

18. The method of claim 16 including making the starting material N-amino,3-methyl tetrahydrothiazine-1,1-dioxide (compound A) by the steps of (a) adding t-butyl carbazate to a solution of a sulfone of structure:

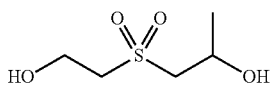

in aqueous sodium hydroxide;

(b) mixing these components at reflux;

(c) extracting the organic layer from the mixture yielding

[(A)]

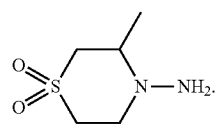

* * * * *